(12) United States Patent
Kerns et al.

(10) Patent No.: US 7,038,766 B2
(45) Date of Patent: May 2, 2006

(54) IDENTIFICATION PARTICLES AND SYSTEM AND METHOD FOR RETROSPECTIVE IDENTIFICATION USING SPECTRAL CODES

(75) Inventors: William J. Kerns, New Brighton, MN (US); Brian Brogger, Blaine, MN (US); Justin L. Esterberg, Andover, MN (US)

(73) Assignee: Microtrace, LLC, Minneapolis, MN (US)

( * ) Notice: Subject to any disclaimer, the term of this patent is extended or adjusted under 35 U.S.C. 154(b) by 408 days.

(21) Appl. No.: 10/023,472

(22) Filed: Dec. 17, 2001

(65) Prior Publication Data

US 2002/0122878 A1 Sep. 5, 2002

Related U.S. Application Data (60) Continuation-in-part of application No. 09/897,553, filed on Jul. 2, 2001, now abandoned, which is a division of application No. 09/283,174, filed on Apr. 1, 1999, now Pat. No. 6,309,690.

(60) Provisional application No. 60/256,209, filed on Dec. 15, 2000.

(51) Int. Cl.
*G06K 9/74* (2006.01)

(52) U.S. Cl. .................................................. 356/71
(58) Field of Classification Search ............ 356/71; 427/7
See application file for complete search history.

(56) References Cited

U.S. PATENT DOCUMENTS

| | | | |
|---|---|---|---|
| 4,146,792 A * | 3/1979 | Stenzel et al. .............. 250/365 |
| 4,238,524 A | 12/1980 | LaLiberte et al. |
| 4,606,927 A * | 8/1986 | Jones .............................. 427/7 |
| 4,767,205 A * | 8/1988 | Schwartz et al. .............. 356/71 |
| 4,812,171 A | 3/1989 | Brettle et al. |
| 4,927,180 A | 5/1990 | Trundle et al. |
| 5,193,854 A | 3/1993 | Borowski et al. |
| 5,289,547 A | 2/1994 | Ligas et al. |
| 5,310,222 A | 5/1994 | Chatwin et al. |
| 5,352,649 A | 10/1994 | Shibahashi et al. |
| 5,380,047 A * | 1/1995 | Molee et al. ................. 283/86 |
| 5,403,039 A | 4/1995 | Borowski et al. |
| 5,490,956 A | 2/1996 | Kito et al. |
| 5,521,984 A | 5/1996 | Denenberg et al. |
| 5,585,425 A | 12/1996 | Kito et al. |
| 5,599,578 A | 2/1997 | Butland |
| 5,630,869 A | 5/1997 | Amon et al. |
| 5,660,925 A | 8/1997 | Cooley et al. |
| 5,673,338 A | 9/1997 | Denenberg et al. |
| 5,751,018 A | 5/1998 | Alivisatos et al. |
| 5,805,245 A | 9/1998 | Davis |
| 5,807,625 A | 9/1998 | Amon et al. |
| 5,826,915 A | 10/1998 | Gregory |
| 5,873,042 A | 11/1998 | Lent et al. |

(Continued)

OTHER PUBLICATIONS

Total Sports Concepts, Tradercode, Internet Page at www-.totalsportsconcepts.com/Authenticity.htlml pp. 1–2, No date.

(Continued)

*Primary Examiner*—Richard A. Rosenberger
(74) *Attorney, Agent, or Firm*—Kagan Binder, PLLC

(57) ABSTRACT

A system and method using reporter elements provides retrospective identification of articles. An article is marked with reporter elements such that the mark has a characteristic spectral response when exposed to energy stimulation. To verify the authenticity of the article, a reader scans the mark containing the reporter elements and obtains a spectral signature. The reader then compares the detected signature to the characteristic signature to determine the authenticity or identity of the marked article.

39 Claims, 8 Drawing Sheets

U.S. PATENT DOCUMENTS

| | | | |
|---|---|---|---|
| 5,864,622 A | 1/1999 | Marcus |
| 5,867,586 A | 2/1999 | Liang |
| 5,873,604 A | 2/1999 | Phillips |
| 5,949,055 A | 9/1999 | Fleet et al. |
| 5,984,366 A | 11/1999 | Priddy |
| 5,986,550 A | 11/1999 | Rapaport et al. |
| 6,005,960 A | 12/1999 | Moore |
| 6,025,200 A | 2/2000 | Kaish et al. |
| 6,030,000 A | 2/2000 | Diamond |
| 6,157,486 A | 12/2000 | Benson, Jr. et al. |
| 6,200,628 B1 | 3/2001 | Rozumek et al. |
| 6,432,715 B1 | 8/2002 | Nelson et al. |
| 6,477,227 B1 | 11/2002 | Kaiser et al. |
| 6,501,825 B1 | 12/2002 | Kaiser et al. |
| 6,647,649 B1 | 11/2003 | Hunt et al. |

OTHER PUBLICATIONS

Sandia National Laboratories, Quantum dots repel each other, researches find, Internet Page www.sandia.gov/media/NewsRel/NR1999/quantum.htlm, pp. 1–4, Dated Aug. 9, 1999.

Spear Thermochromic Inks, www.spearinc.com/thermink.htm, Jun. 10, 1998.

DynaHeat Plastisol "Color Change" Thermochromic Inks, www.interactivecolors.com/plasinf1.htm, 1995.

CTI Thermochromic "Color Change" Plastisol, www.interactivecolors.com/plscolor.htm, 1995.

Security Inks, Thermochromic Ink, http://ourworld.compuserve.com/homepages/Grant_Cari_Fairely/security.htm, Dec. 7, 1998.

NVE Corporation, Advanced Technology Group, www.nve.com/advtech.html.

NVE Corporation Products, www.nve.com/product.html,.

NVE Sensor Products Business Group, www.nve.com/sbindex.html.

* cited by examiner

IDENTIFICATION PARTICLES AND SYSTEM AND METHOD FOR RETROSPECTIVE IDENTIFICATION USING SPECTRAL CODES

This application is a continuation-in-part of U.S. Ser. No. 09/897,553, filed Jul. 2, 2001 now abandoned which is a divisional application of Ser. No. 09/283,174 now U.S. Pat. No. 6,309,690, issued Oct. 30, 2001 and filed Apr. 1, 1999 and a continuation of provisional application U.S. Ser. No. 60/256,209, filed Dec. 15, 2000. Priority is claimed to these applications.

FIELD OF THE INVENTION

The present invention relates generally to the marking of articles for retrospective identification or authentication and more particularly to systems and methods for marking an article with spectrally coded material and using the characteristic spectral signature of the coded material to retrospectively identify or verify authenticity of marked articles.

BACKGROUND OF THE INVENTION

Authentication and identification of articles is of great concern in a number of arenas. For example, customs agents attempt to stop shipments of counterfeit goods when they enter the country. To do so, they must be able to distinguish between genuine or authorized goods and counterfeit or unauthorized goods. Attempts have been made to mark authorized goods and/or their shipment containers and to provide a system for officials to use the marks to confirm the authenticity of the goods.

Many applications for authenticity-verifying or source-verifying technology require or are benefited from solutions which are easily implemented by a person "in the field". Other applications are benefited from solutions which are easily automated to allow fast yet more complete, rather than spot-checked, reviews of larger numbers of articles.

What has been needed has been an authentication system with protections against counterfeiting and with ease of use and access for customs officials, law enforcement, and other interested persons to verify the authenticity of articles. The system and method should allow the user several different methods to authenticate or identify an item. A needed system and method should have varying levels of security, such that a first magnified "eyeball" review provides some level of assurance that the goods are authentic; additional covert features which are more difficult to verify and more difficult to counterfeit offer further levels of security. Further, the system should be conducive or adaptable to "in the field" applications using hand held or portable verification or reading equipment. Still further, it is advantageous for an authentication system to be adaptable to automation, such that articles can be scanned and authenticated quickly and accurately while minimizing human labor.

SUMMARY OF THE INVENTION

In a preferred system and method according to the present invention, one or more reporter elements is applied to an article, item or a label for which retrospective identification is desired. Upon excitation or stimulus, such as from an energy source, the reporter elements yield a spectral "signature" that characterizes the reporter elements' response to the stimulus. To verify the authenticity of the subject article, the microparticle mark is scanned with a device that "reads" the spectral signature of the reporter elements and determines whether the detected signature matches the predefined signature. The reader displays an indication that the article is authenticated.

In another embodiment, the spectral signature of reporter elements to be applied to an article is read, and is translated via an algorithm to a printable code, such as an alphanumeric code or a bar code, that is then printed on the article or on the label bearing the mark. The detector uses the same algorithm to decipher the code and displays this deciphered code, and the user then reads the code displayed on the reader device and compares that to the printed code. If the deciphered code matches the printed code, then the article is authentic. As an additional feature, a serial number or otherwise unique code is added to the deciphered code from the spectral signature. In this manner, each marked article is uniquely identifiable by its serial number, as well as batch identifiable by its spectral code.

Preferably, one or more reporter elements are incorporated into one or more layers of a microcoded particle or are applied in conjunction with a microcoded particle.

The system and method of the present invention can be used in conjunction with the pattern recognition in the manner described in U.S. Ser. No. 09/283,174, filed Apr. 1, 1999, issued as U.S. Pat. No. 6,309,690, incorporated herein by reference in its entirety.

In another preferred embodiment, the microparticles have distinctly colored layers and the sequence of the colored layers forms a code that is assigned to a particular meaning, such as the source or identity of goods marked with the particles. The colors of the microparticles may be selected advantageously to have some common association to the article.

In another preferred embodiment, the microparticles have indicia on or below the surface of the particle. Preferably the indicia is embossed, laser etched, photo reduction, or the like.

These preferred embodiments enable a variety of methods of "interrogating" the microcoded marks to confirm the authenticity of the article. Some of the embodiments have at least one level of security that can be viewed and assessed with simple magnification. Other embodiments require exposure of the mark to an energy stimulus, such as temperature changes, light, or electric current induced by magnetic field.

These preferred embodiments enable varying degrees of security against counterfeit.

BRIEF DESCRIPTION OF THE DRAWINGS

An exemplary version of a microcoded mark and a system and method for authenticating articles is shown in the figures, wherein like reference numerals refer to equivalent structure throughout, and wherein:

FIG. 4 is a schematic illustration of a system and method for interrogating a label to determine its authenticity, where the label or article has been marked in accord with the system and method of FIG. 1a;

DETAILED DESCRIPTION OF PREFERRED EMBODIMENTS

Figure 1:
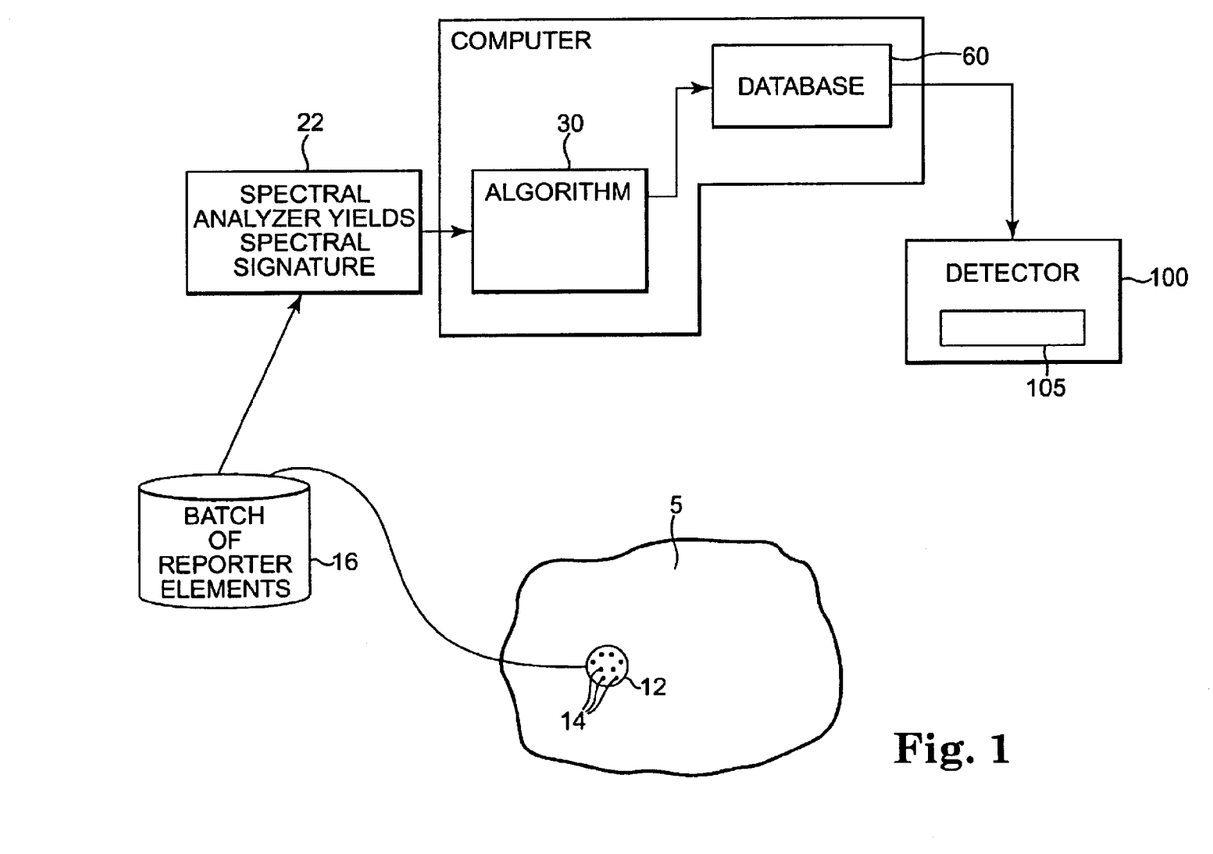
FIG. 1 is a schematic illustration of a system and method for marking an article for retrospective identification with reporter elements.

A preferred system and method for retrospective identification of an article 5 or a container of articles using spectral signatures according to the present invention is illustrated schematically in FIGS. 1–6. FIG. 1 illustrates a magnified mark 12 that is generally undecipherable to the naked eye. That is, it may be apparent that the mark is present, but the detailed aspects of the mark are not visible without magnification or digital imaging. The mark 12 incorporates reporter elements 14. A reporter element 14 is any atom, molecule, crystal, polymer or other compound or the like that interacts with a form of energy, such as light, to give a detectable light emission or absorption response. Reporter elements 14 are described in greater detail below in the section entitled "Reporter Elements". Examples of the many manners in which reporter elements 14 can be incorporated into the mark 12 and the materials that can be used for reporter elements 14 will be described in greater detail below.

Figure 1A:
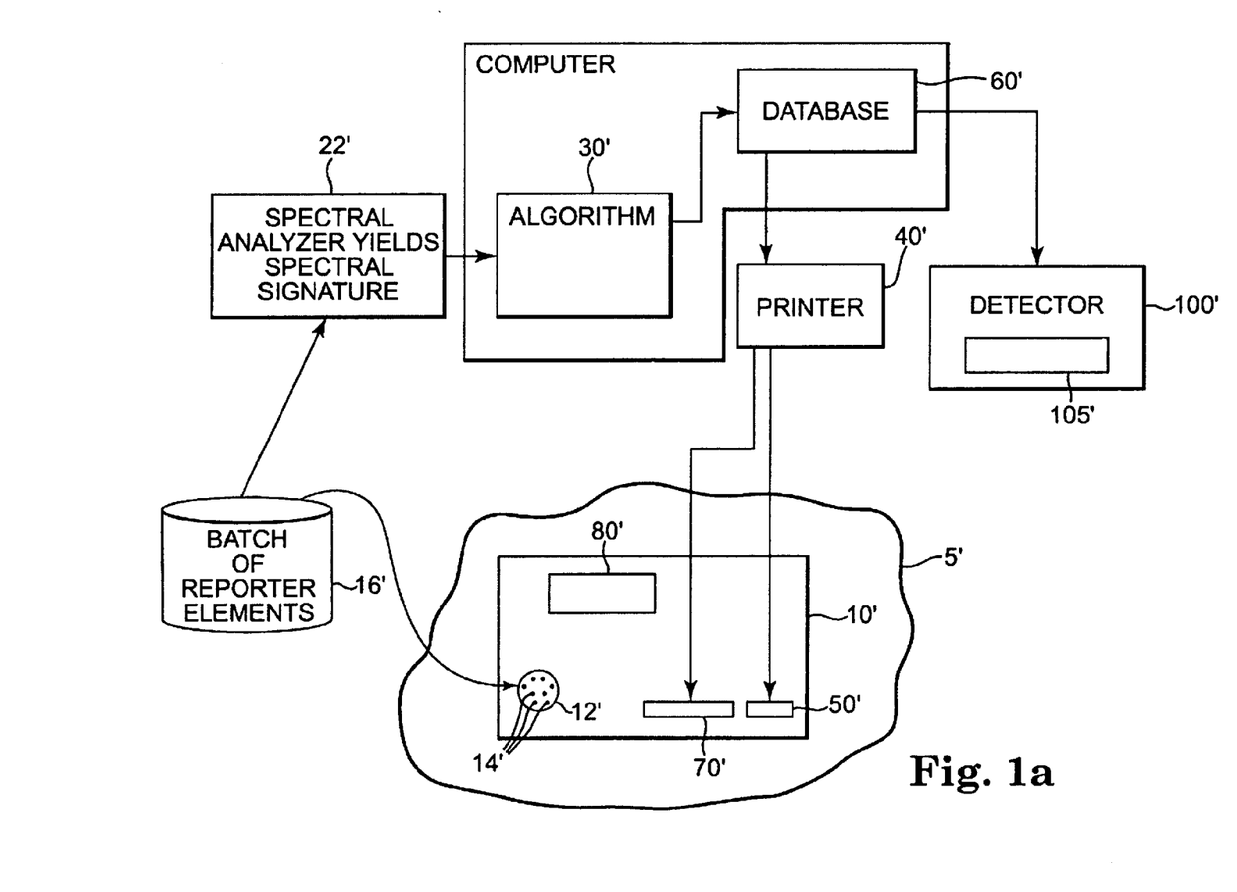
FIG. 1a is a schematic illustration of a system and method for marking an article for retrospective identification with reporter elements and a printable code computed from the spectral response of the reporter elements.

The mark 12 can be applied to, affixed to, mixed into, or otherwise connected to the article 5 to be retrospectively identified. Of course, the manner of that connection will be determined in many cases by the nature of the article 5. For example, if the article 5 is a powdered material, such as that used in an explosive compound, the reporter elements 14 can be directly mixed into the powder. Alternatively, as will be described below, the reporter elements 14 can be embedded within a microcoded particle, and these microcoded particles can be mixed into the explosive powder. For other applications, it will be desirable to affix the reporter elements (within a microcoded particle or alone) to a label that is adhered to an article. Still further, it may be desirable to incorporate the reporter elements (within a microcoded particle or alone) in an adhesive or an ink, or the like which is then applied to a label or article, as depicted in FIG. 1a. Microcoded particles or microparticles are described in greater detail below in the sections entitled "Microcoded Mark", and the incorporation of reporter elements within a microcoded particle is described below in the "Reporter Elements" section.

Preferably reporter elements of one or more types are mixed to yield a batch of "spectral code" 16. Each type of reporter element has a characteristic absorption/emittance response to energy stimulation. Variable concentrations of reporter elements can be used to provide unique emission intensities. The spectral signature of a mix of two or more elements contains the additive combination of the spectral response signatures of each included element or type. Typically, this additive combination yields a response and peak over one wavelength range for one element, and a response and peak over another wavelength range for a second element, and so on. In other words, the types are chosen such that their responses are distinct; each type responds across a different wavelength than other type or types within the batch.

Figure 2:
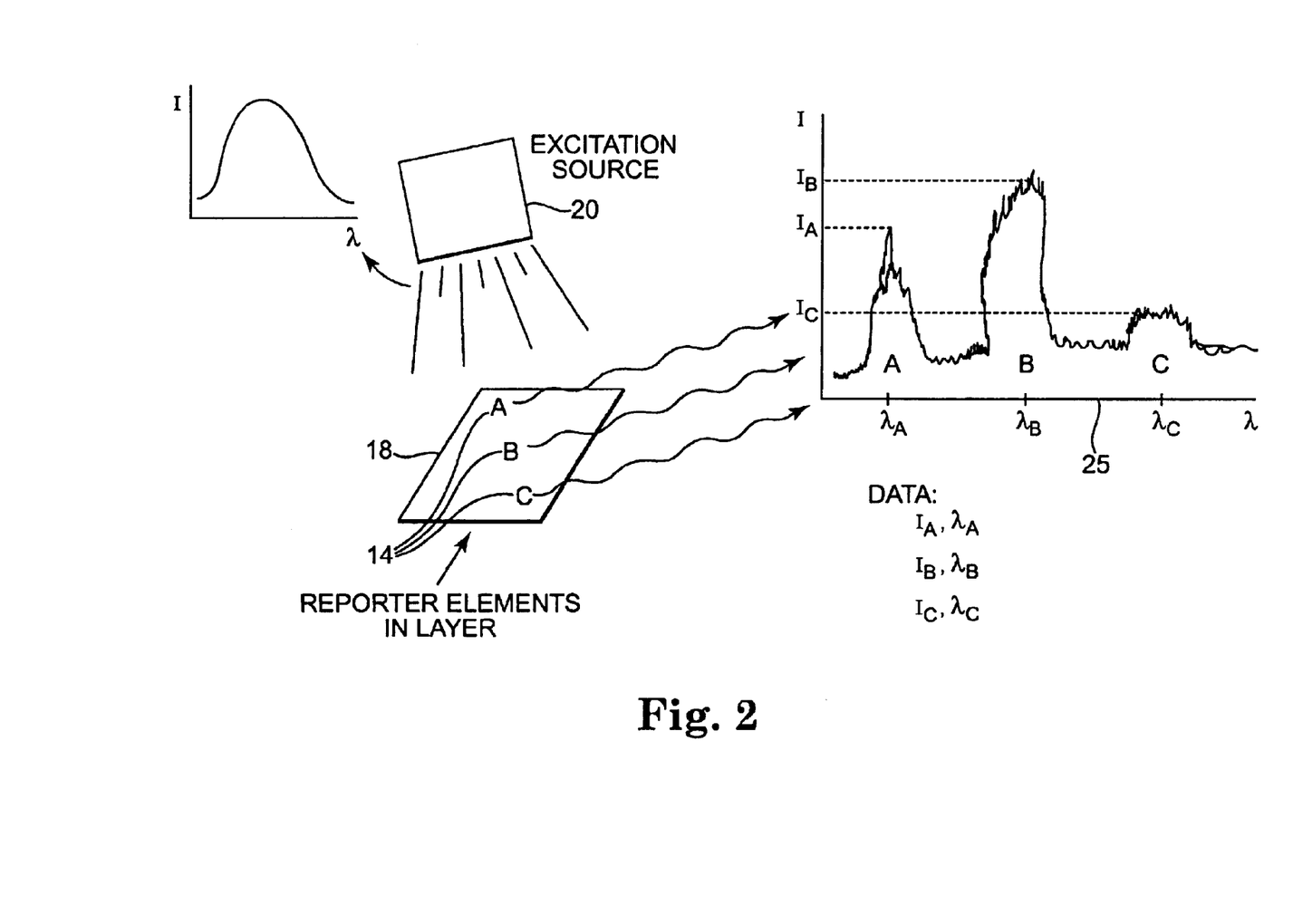
FIG. 2 is schematic illustration of the generation of a spectral signature for spectral code containing three types of reporter elements.

As illustrated in FIG. 2, a sample 18 of the batch of spectral code 16 is exposed to an energy excitation source 20, such as light or heat, to which the reporter elements A, B, and C 14 respond. A spectral analyzer 22 reads the response of the reporter elements 14 and generates a spectral signature 25 displayed in a graph showing intensity as a function of wavelength. Alternatively, the analyzer generates a spectral signature displayed in a graph of intensity as a function of frequency or wavelength. As another alternative, the spectral signature could be displayed in a graph of the sum of two or more of these functions or other mathematical manipulation of any of these signatures or combinations of the signatures.

Each type of reporter element 14 shows a maximum or peak response within or across a predetermined range of wavelengths. In the illustrated example, three types of reporter elements, A, B and C, yield three corresponding maximum intensity peaks $I_A$, $I_B$ and $I_C$ at wavelengths $\lambda_A$, $\lambda_B$ and $\lambda_C$, respectively. The intensity of the response of each type of reporter element 14 depends upon its concentration in the sample 18. Upon interrogation, a detector is used to observe the spectral response of mark made of sample 18. The detector preferably provides an indication of whether the detected signature meets the pre-defined signature for sample 18.

The system and method can use either or both of the parameters of wavelength and intensity to characterize the spectral signature of a sample 18. In other words, the signature might be defined such that an intensity peak must be exhibited at a particular wavelength or between a range of wavelengths, but the actual values of the intensity might be ignored. Alternatively, for added security or precision in identification, the signature might be defined such that a particular intensity maximum must be exhibited at a specified wavelength or within a range of wavelengths. As another alternative, the intensity alone might be used: i.e., if the intensity of the response is not at or sufficiently near a specified intensity value, then the conclusion can be drawn that the specified reporter element is not present in the concentration required of an authentic sample.

For some types of reporter elements 14, other aspects of a spectral signature can be used. For example, the spectral response of fluorescent or phosphorescent materials is time-dependent, with the maximum intensity of its response diminishing over time after the removal of an energy stimulus. Thus, these materials have a characteristic half-life. The time-dependent signature can be characterized through relatively rapid serial analysis of the emission signal.

An optional feature which offers additional security advantages includes the transposition of the spectral signature into an alpha-numeric code or other type of printable code, such as a bar code. This is illustrated in FIG. 1a in conjunction with an application involving a mark on a label 10', though this printed code aspect might also be used in conjunction with applications that do not involve a label. As illustrated in FIG. 1a, the spectral signature 25' is filtered through an algorithm 30' to transpose the signature 25' into a printable code 50', such as an alpha-numeric code or a bar code. A printer 40' prints this printable code 50' on the label 10'. Further, the printable code 50' is stored in a database 60' in conjunction with a description of the goods on which the printable code 50' is placed. Optionally, the database 60' may assign a unique identifier 70', such as a serial number, to the article and the printer 40' can print that unique identifier 70' on the label 10'. In one embodiment, the serial number 70' and the printable code 50' are joined into one string (alphanumeric, bar-code or other) that is printed on the label 10'. Optionally, the label 10' also includes human-readable written identification or description 80' of the goods.

Figure 3:
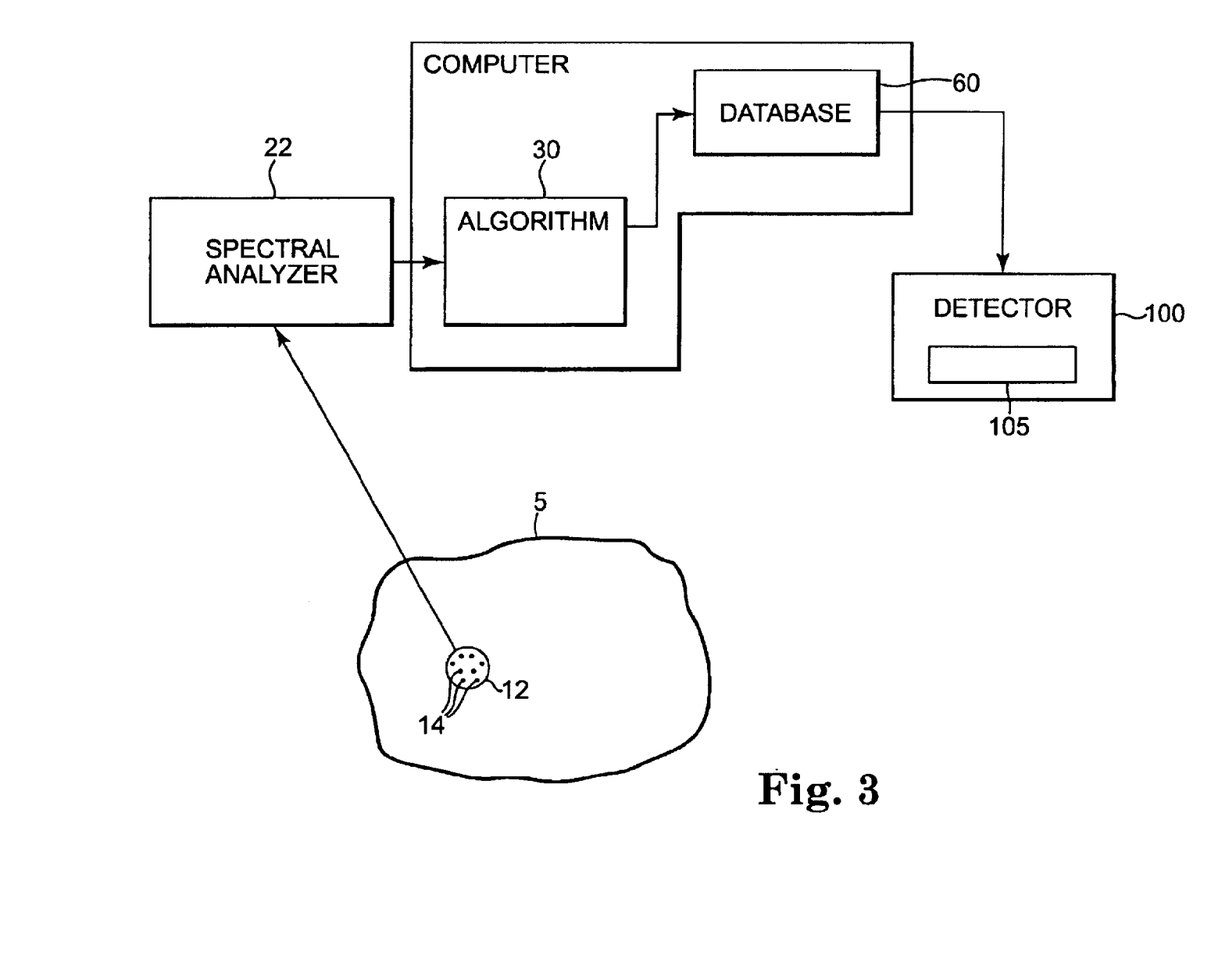
FIG. 3 is a schematic illustration of an alternate version of the system and method illustrated in FIG. 1.

FIG. 3 illustrates an alternative order for initial steps in the marking of an article. In the FIG. 3 embodiment, the mark 12 is first applied to the article 5 (or on a label 10') and then scanned by a spectral analyzer 22 to determine the spectral signature of the mark 12, or more specifically of the reporter elements 14 in the mark 12. The rest of the system and process depicted in FIG. 3 is the same as that depicted in FIG. 1 and described above.

Figure 4:
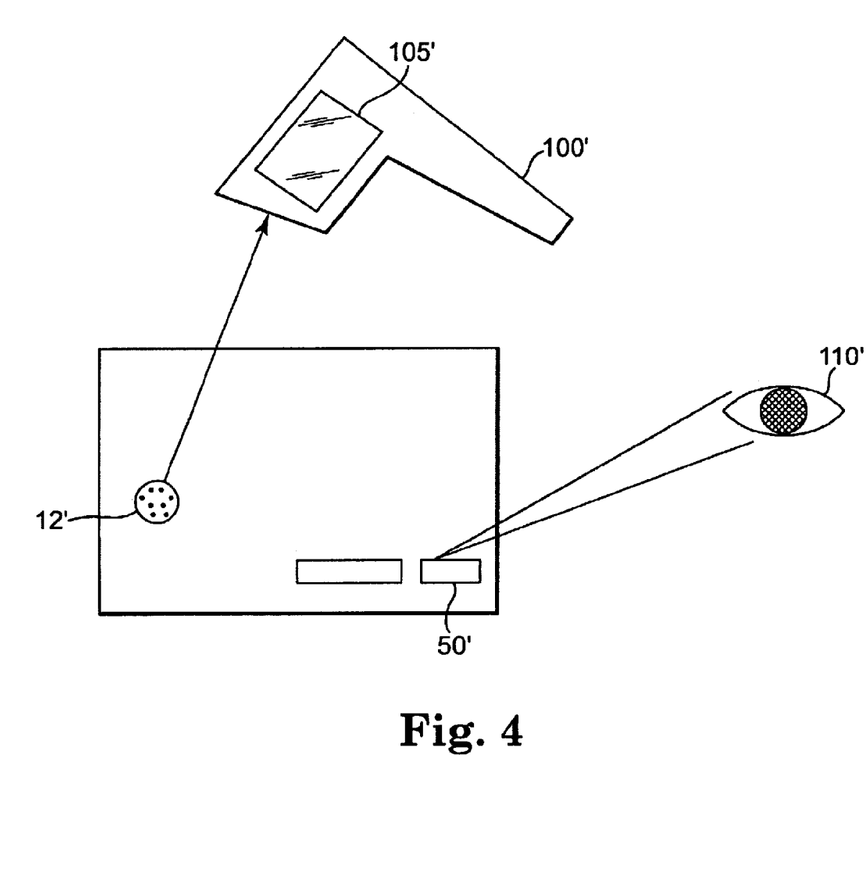
Figure 5:
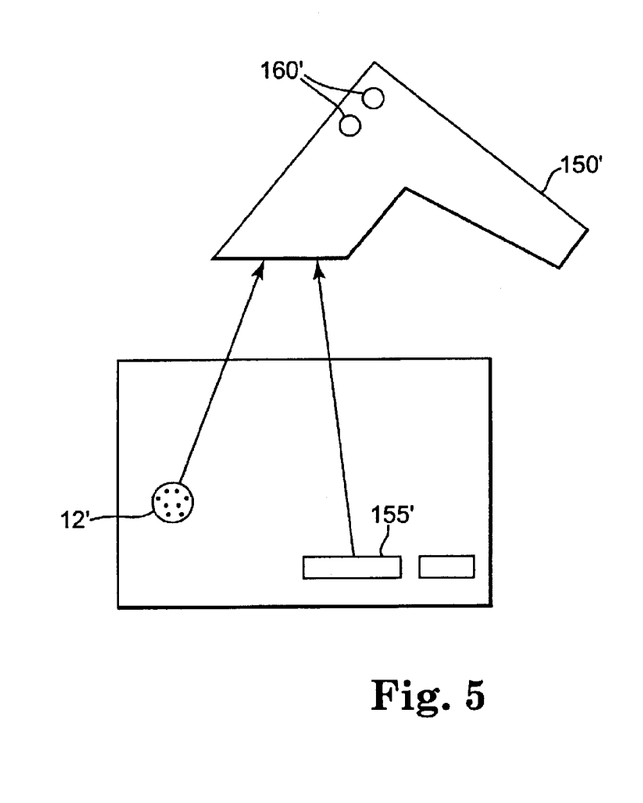
FIG. 5 is a schematic illustration of a system and method for interrogating a label to determine its authenticity, where the label or article has been marked in accord with the system and method of FIG. 1a and with a bar code.

FIGS. 4 and 5 illustrate ways that an article 5', marked in the manner illustrated in FIG. 1a, can be interrogated to determine the authenticity of the article 5'. As shown in FIG. 4, a reader or detector 100' images the mark 12' and computes the printable code 50' by performing the designated algorithm 30' on the spectral signature. A display 105' on the reader 100' displays the computed code. The user 110' views and compares the computed code with the code 50' printed on the article or on a label 10' affixed to the article. In the illustrated case, the mark and code both appear on a label 10' which is coupled with the article to be identified. If the codes match, then the article is legitimate. Preferably, in a label configuration, the label 10' is tamper-evident, such that if a legitimate label is removed from its original location, the mark 12' is destroyed or altered, such that spectral analysis and decoding of the altered mark 12' will not yield a computed code that matches the printed code 50'.

In another embodiment, illustrated in FIG. 5, a reader 150' scans the mark 12' and a a serialized barcode 155' printed on the article or a label affixed to the article. If these components "match", then the reader 150' gives an indication of a match, such as with an indicator light 160'. The components match if they are stored in conjunction with one another in the database 60'.

FIGS. 4 and 5 illustrate analysis via a generally portable device, with the mark 12' being reviewed without disturbing its attachment to the article. In some cases, however, it may be advantageous to extract the reporter elements to perform other types of analysis not conducive to portable equipment or to "in the field" methods or technology.

Technology and methods that can be used for spectral analysis are well known to those of skill in the art, and include, for example: chromatography, mass spectroscopy, nuclear magnetic resonance, infrared spectroscopy, ultraviolet/visible spectroscopy, flame ionization, electrical analysis, thermal analysis, hybridization assays, gel electrophoresis.

Reporter Elements

As described above, a reporter element can be any molecule, crystal, atom or compound, including polymers, that, when stimulated by energy, yield a detectable energy, mass or other response. For light responsive reporter elements, materials can be used which are responsive to any desired frequency or wavelength. The response of the reporter element is dependant upon the material of the reporter element as well as the energy stimulus provided but typical responses include fluorescence, phosphorescence, upconverting phosphorescence, absorption and emission.

As will be understood, the material used for the reporter element, the appropriate energy stimulus, and the response of the reporter element are copescetic. The following chart provides examples of materials, energy stimuli and responses:

| Material-Any material from the following family of materials: | Energy Stimulus | Response |
| --- | --- | --- |
| Flourescents | Light | Light (Fluorescence) |
| Phosphorescents | Light | Light (Phosphorescence) |
| Upconverting phosphorescents | Light | Light |
| Photochromics | Light | Light of predetermined wavelength |
| Thermochromics | Heat/Cold | Light |
| Electrochromics | Electric current | Light |
| Infrared fluorescents | Light in infrared wavelengths | Light (Fluorescence) |
| Infrared phosporescents | Light in infrared wavelengths | Light (Phosphorescence) |
| Near-infrared fluorescents | Light in near-infrared wavelengths | Light (Fluorescence) |
| Semi-conducting nanocrystals (e.g. from the group II–VI such as cadmium selenide CdSe, magnesium selenide MgSe, calcium selenide CaSe, barium selenide BaSe, zinc selenide ZnSe) | Light | Light |
| Magnetic resonance molecules | Magnetic field | Nuculear magnetic resonance (NMR) frequencies |
| Isotopic isomers or really any atom, ion, molecule | Electrical energy | Mass detection |

The semiconducting nanocrystal family offers advantages of stability (i.e. increased shelf life), relatively narrow emission spectra, relatively broad excitation spectra, and can be excited without laser-generated light.

Figure 6:
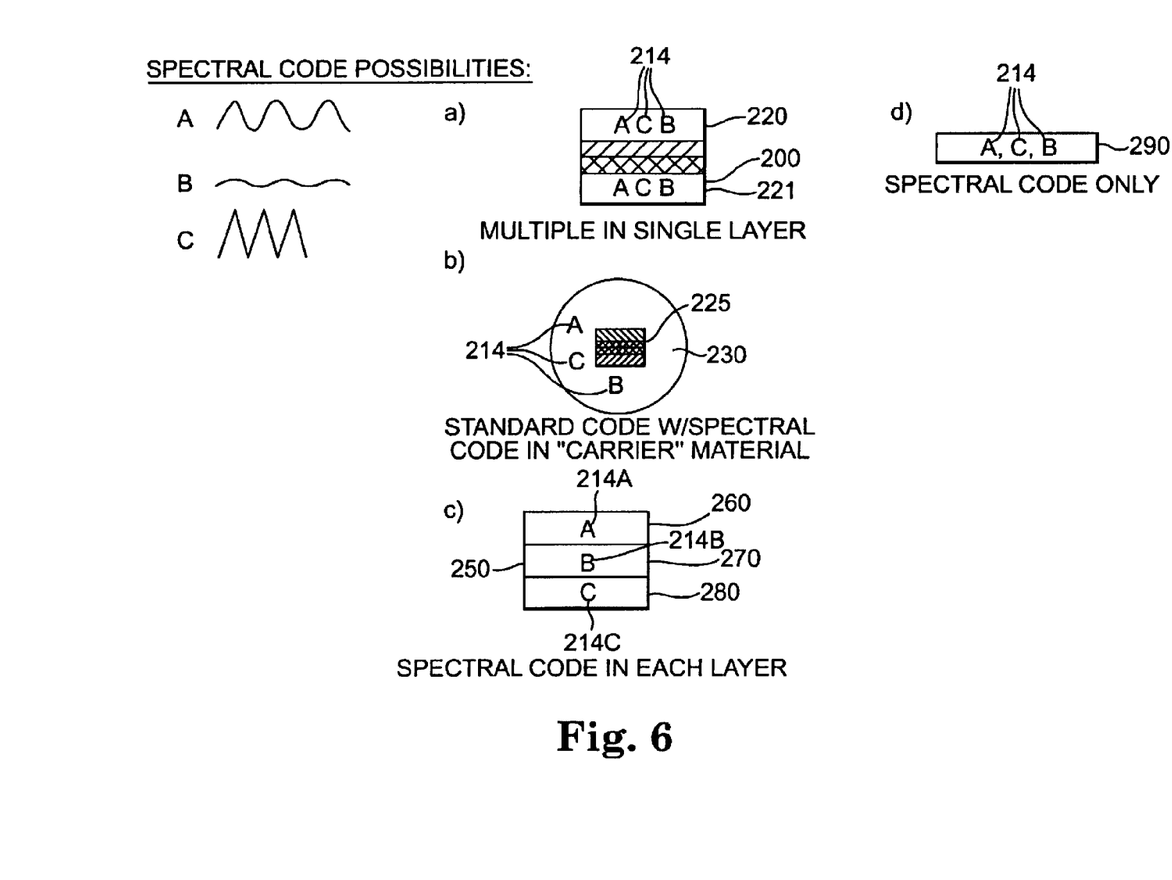
FIGS. 6a–6d are schematic illustrations of alternate arrangements for incorporating reporter elements in one or more layers of a microparticle or microcoded particle.

As illustrated in FIG. 6, reporter elements 14 can be implemented in combination with a microcoded particle or substrate in a variety of ways to form an identification particle. Generally, a microcoded particle is a multilayered particle. Microcoded particles are described in greater detail below.

FIG. 6a shows a microcoded particle 200, with reporter elements 214 entrained in the outer layers 220 and 221 of the particle 200.

FIG. 6b shows an arrangement wherein reporter elements 214 are entrained in carrier material 230, such as adhesive, ink or other material, in which microparticles 225 are entrained, but where the reporter elements 214 are separate and distinct from the microparticles 225.

FIG. 6c shows an arrangement wherein one type of reporter element is incorporated into one layer of a microparticle 250. More specifically, reporter element 214A is entrained in a first layer 260; reporter element 214B is entrained in second layer 270; and reporter element 214C is entrained in third layer 280.

FIG. 6d shows an arrangement wherein a single layer substrate 290 contains the reporter elements 214, preferably of two or more types 214A, 214B, 214C. In some applications, it may be advantageous to add embossing of a bar code or other indicia to the surface of the substrate for additional identification properties.

While all of these examples of FIGS. 6a–6d illustrate the incorporation of three types of reporter elements, it will be understood that any number of reporter elements can be used. For the example of FIG. 6c, the layers could contain the same type of reporter element, but in varying concentrations in adjacent layers. Further, the microcoded particle might contain one or more layers without any reporter elements therein.

The Microcoded Mark

The use of microparticles for the retrospective identification of articles is known from U.S. Pat. Nos. 4,053,433 and 4,390,452, incorporated herein by reference, and from other sources. Such particles may be used for the identification of a wide variety of items. Each microparticle includes a sequence of visually distinguishable dyed and/or pigmented layers. The microparticles are "coded" in the sense that particular color sequences in the particles are assigned to a particular meaning, such as the source of the item on which the particles are placed. Typically, microparticles are not "readable" to the naked eye, i.e. the particles must be magnified for the layer sequence to be discerned.

Figure 7:
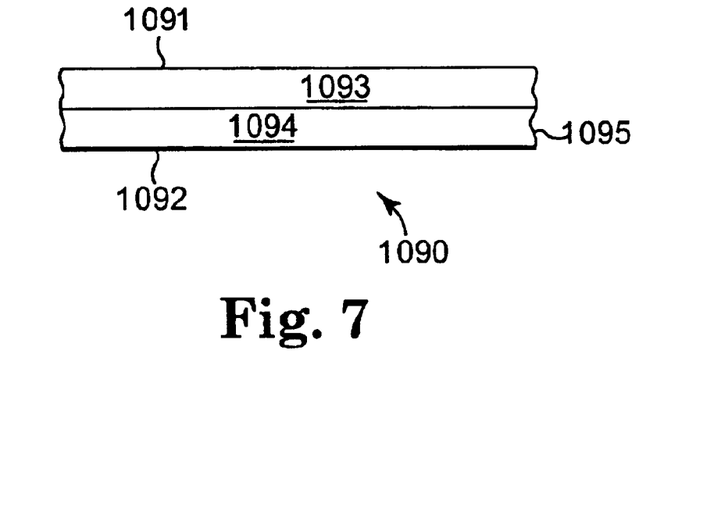
FIG. 7 is a an enlarged side view of a microparticle used in accordance with the present invention.

FIG. 7 shows a microparticle 1090. The particle 1090 has top and bottom surfaces 1091 and 1092, with two or more layers 1093, 1094 therebetween. An edge 1095 extends between the top and bottom surfaces and circumscribes the particle. The edge 1095 is generally irregular. While the depicted microparticle has only two layers, the microparticle may contain any number of layers.

In a preferred embodiment, energy-sensitive materials, such as thermochromic or photochromic materials, may be used for one or more of the layers. An energy-sensitive material has different optical properties under different conditions. For example, a thermochromic material is transparent in one temperature range, but opaque outside of that range. Photochromic material can be transparent or one color under white light of a range of frequencies, but a different color when exposed to light outside of that range of frequencies. Use of energy-sensitive material for all of the layers aids in making the microcoded mark covert. That is, if the layers are of thermochromic material having the property of being transparent at room temperature, and if the particles are entrained in a generally transparent adhesive or epoxy, then the microcoded mark will be generally covert at room temperature. The mark and the sequence of its colored layers can be revealed by exposing the mark to an elevated or decreased temperature, depending upon the predetermined properties of the thermochromic material.

In another preferred embodiment, near-infra-red-frequency material is used in the microparticle. Such material flouresces when exposed to infra-red light. Use of this material aids in making the microcoded mark covert. Currently, known infra-red materials lose their responsiveness over time upon exposure to UV light. Therefore, in a preferred embodiment of these microparticles, a near-infra-red-frequency layer is covered by or sandwiched between energy sensitive layers that are opaque at typical indoor ambient temperatures to protect the near-infra-red material from exposure to UV light under typical temperature conditions, thereby prolonging the life of the near-infra-red material.

In another preferred embodiment, magnetic materials or other materials that exhibit unique NMR spectrum are used in the microparticle.

In another embodiment, the microcoded particle may be a one or more layers that may be clear or colored and may include indicia thereon. The indicia may be produced by laser etching, embossing, photo reduction, or the like. Reporter elements may be entrained in the layer or substrate.

Figure 8:
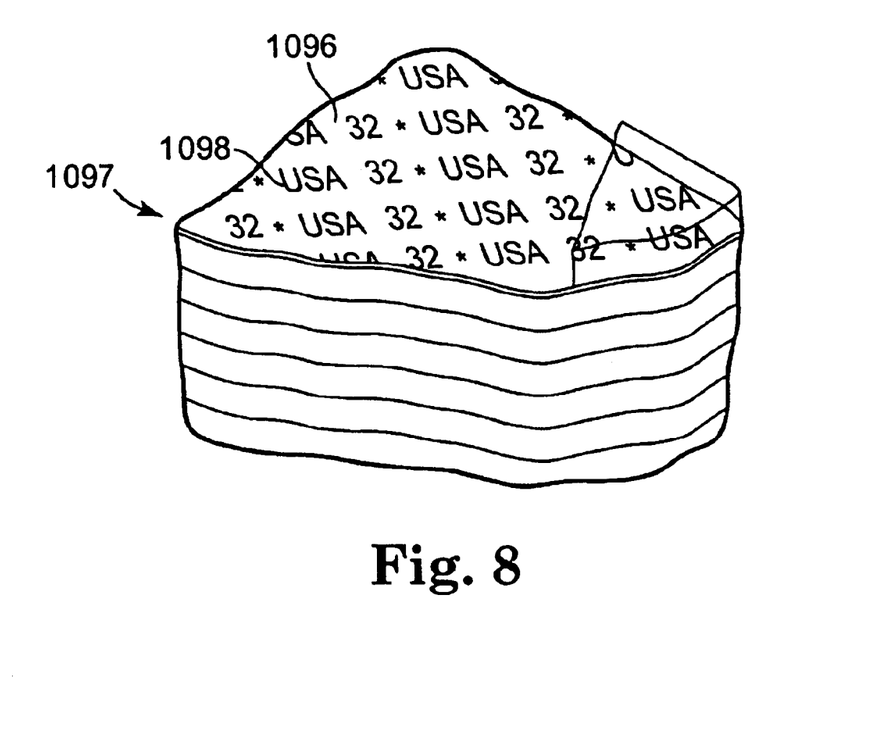
FIG. 8 is an enlarged perspective view of an embodiment of a microparticle used in accordance with the present invention.

In another preferred embodiment, illustrated in FIG. 8, an outer surface or visible layer 1096 of the multi-layered microparticle 1097 bears indicia 1098, such as alpha-numeric characters, patterns, abstract images or the like. The indicia are preferably registered. A typical method of forming microparticles bearing indicia yields slightly recessed indicia. Such a method involves laser etching or embossing of the indicia onto the outer surface of the microparticles. Another such method is described in U.S. Pat. No. 4,390,452. To enhance the visibility of the recessed indicia, the method may also include a step of applying a curable ink to the indicia-bearing surface, wiping the ink away, leaving ink settled in the recesses, while leaving the un-recessed area substantially ink-free. When a curable ink is used, the particle can then be cured, and the ink will solidify and the ink-filled indicia are then more easily discernable. For example, inks that cure upon exposure to ultraviolet can be used.

The "code" of the microparticles aids in the retrospective identification of the article because a particular code can be assigned to a specific article, application or customer. The code is retired, and particles bearing this sequence or indicia will not be used in a conflicting manner. Retrospectively, the microcoded mark can be viewed under magnification and, using information stored in a database, matched with the information relating to that particular color sequence or indicia revealing that the article matches the article to which that sequence is assigned.

The Detector

A reader or detector 100, 100' or 150' incorporates hardware that links it to the computer on which the algorithm 30 and database 60 or algorithm 30' and database 60', respectively, are stored so that it can access the relevant algorithm 30 or 30', respectively, as well as data from the database 60 or 60', respectively, regarding the subject goods, such as a textual description or serial numbers. This link can be made via the internet or via hardwire or any other method of transferring digital information. Preferably, security features allow access to the database and algorithm only to selected users.

The detector can also be used to read barcodes on labels, identify the location of reporter elements in a microcoded particle. The detector may include a video monitor to view an image of the area being examined or display the results of each test.

The preferred detector contains an excitation source to provide the stimulus needed to generate the signature response from the reporter elements.

One embodiment of the detector includes a cycling mechanism such that the excitation stimulus and response detection are pulsed or timed. This offers particular advantage when used to detect half-life signatures.

Preferably, a detector is capable of detecting a wide range of wavelengths of light to accommodate a variety of types of reporter elements. Filters, photomultipliers, resistors and the like can be used to accomplish this.

Preferably, the detector has circuitry that allows for the analysis of the spectral signature in a variety of ways. At a basic level, if all types of expected reporter elements are present, the detector yields a "yes" or "no" answer. A more sophisticated detector yields more detailed analysis, such as indicating the presence of individual types of reporter elements.

The detector can indicate whether the detected reporter elements "match" the expected, predefined signature in various ways. For example, colored LEDs can be incorporated. Red and green LEDs can be used to indicate a yes/no determination. Alternatively, several LEDs of various colors can correspond to each colored layer in a microcoded particle.

Although an illustrative version of the method and system is described below, it should be clear that many modifications to the method and system may be made without departing from the scope of the invention as expressed in the appended claims.

Throughout this description, the following terms include the meanings ascribed to the term by those of ordinary skill in the art and includes meanings now understood and those yet to be discovered or applied; the terms include, but are not limited to, at least the following illustrative meanings:

Data means textual, numeric, graphic, symbolic or any other information.

Input device includes a keyboard, mouse, track ball, stylus, touch-sensitive screen, touch-sensitive cursor or mouse pad, or voice receiver and recognition apparatus/software or any other device now known or yet to be developed for a human to interact with a digital storage medium to input or access data stored therein.

Storage medium means any method of storing information for later use, particularly in connection with digitized information, including but not limited to a floppy disk, a hard drive, digital tape, and compact disk.

Network means any connection between two computers by which one computer can send or access information stored on another computer, including but not limited to hard-wired connection, modem/phone line connection, modem/satellite connection, and RF connection.

Database means an organization and storage system for records, wherein one or more pieces of information are stored for each record.

Indicia or indice means numeric characters, alphanumeric characters, Roman numerals, abstract images, barcodes, logos, patterns and the like. Indices may be serialized or not serialized.

Label means an image-bearing medium, whether optical or mechanical, including but not limited to paper, foil, or multi-layer configurations.

What is claimed is:

1. A method of determining if an article includes a taggant that comprises coded information, said method comprising the steps of:
   a) providing an article;
   b) subjecting the reporter element to energy stimulation to determine whether the article incorporates a taggant particle comprising at least one reporter element that emits a spectral signature responsive to energy stimulation;
   c) detecting the reporter element's spectral signature response to the stimulation, wherein said spectral signature provides a first code; and
   d) if the article incorporates the at least one reporter element, determining if the taggant particle further comprises a second constituent that provides a second code.

2. A method according to claim 1, wherein the second constituent comprises an encoded particle comprising a sequence of colored layers, wherein the sequence of the colored layers provides the second code.

3. A method according to claim 2, wherein the at least one reporter element is incorporated into the encoded particle.

4. A method according to claim 1, wherein the at least one reporter element is incorporated into the second constituent.

5. The method for retrospective identification, according to claim 1, wherein said first code is derived from information indicative of how the intensity of a spectral signature of a reporter element varies with frequency of stimulating energy.

6. The method for retrospective identification, according to claim 1, wherein said first code is derived from information indicative of how the intensity of a spectral signature of a reporter element varies with wavelength of stimulating energy.

7. A method of marking an article for retrospective identification, comprising the steps of:
   a) providing a taggant particle comprising at least one reporter element and an encoded particle, wherein the at least one reporter element is entrained in a layer of a particle comprising a sequence of colored layers, wherein a spectral signature of a reporter element is associated with a first code and the sequence of colored layers is associated with an independent, second code; and
   b) attaching the microcoded particle to the article.

8. A method according to claim 7, further comprising the steps of recording said first and second codes in a database in conjunction with information identifying the article.

9. A method according to claim 7, further comprising the steps of assigning a unique identifier to the article and attaching said unique identifier to said article.

10. A method according to claim 9, wherein said unique identifier is a serialized bar code.

11. A method according to claim 10, wherein said code and said bar code are printed on a label.

12. A method according to claim 7, wherein a plurality of reporter elements are incorporated into the encoded particle.

13. A method according to claim 1, wherein said reporter elements comprise two reporter elements having different spectral responses to energy stimulation.

14. Method of claim 7 wherein at least two different types of reporter elements are entrained within one layer of the encoded particle.

15. Method of claim 7 wherein one or more different reporter elements are entrained in two or more layers of the encoded particle.

16. An identification particle for use in retrospective identification, comprising:
   a) an encoded particle comprising a sequence of colored layers; and
   b) at least one reporter element entrained in a layer of said encoded particle, wherein a first code is associated with the at least one reporter element and a second code is associated with the sequence of colored layers.

17. The identification particle according to claim 16, wherein a reporter element resides in a first surface layer of the encoded particle.

18. The identification particle according to claim 17, wherein a reporter element resides in a second surface layer of the encoded particle.

19. The identification particle according to claim 16, wherein more than one reporter element is entrained in a layer of the encoded particle.

20. The identification particle according to claim 16, wherein one reporter element resides in one layer of the encoded particle, and another reporter element resides in another of the layers of the encoded particle.

21. The identification particle according to claim 16, wherein each layer of the encoded particle contains one reporter element, and each reporter element is distinct from the others in the encoded particle such that each generates a different characteristic spectral response to energy stimulation.

22. The identification particle according to claim 16, wherein a layer of said encoded particle contains no reporter element.

23. The identification particle for use in retrospective identification according to claim 16, wherein said reporter element is fluorescent.

24. The identification particle for use in retrospective identification according to claim 16, wherein said reporter element is phosphorescent.

25. The identification particle for use in retrospective identification according to claim 16, wherein said reporter element is upconverting phosphorescent.

26. The identification particle for use in retrospective identification according to claim 16, wherein said reporter element is photochromic.

27. The identification particle for use in retrospective identification according to claim 16, wherein said reporter element is thermochromic.

28. The identification particle for use in retrospective identification according to claim 16, wherein said reporter element is electrochromic.

29. The identification particle for use in retrospective identification according to claim 16, wherein said reporter element is infrared fluorescent.

30. The identification for use in retrospective identification according to claim 16, wherein said reporter element comprises semi-conducting nanocrystals.

31. The identification particle for use in retrospective identification according to claim 16, wherein said reporter element comprises an isotopic isomer.

32. The identification particle for use in retrospective identification according to claim 16, wherein said first code is associated with a detectable mass of a reporter element.

33. The identification particle for use in retrospective identification according to claim 16, further comprising a bar code embossed on a surface layer of the encoded particle.

34. The identification particle for use in retrospective identification according to claim 16, further comprising indicia embossed on a surface layer of the encoded particle.

35. A method of forming an identification particle for use in retrospective identification, comprising the steps of:
   a) forming an encoded particle comprising a sequence of colored layers;
   b) entraining at least one reporter element in a layer of the encoded particle;
   c) associating a first code with the at least one reporter element; and
   d) associating a second code with the sequence of colored layers.

36. A method of marking an article for retrospective identification, comprising the step of incorporating a taggant particle into the article, wherein the taggant article comprises (a) at least one reporter element that emits a spectral signature responsive to energy stimulation, wherein said spectral signature provides a first code; and (b) a second constituent that provides a second code.

37. The method of claim 36, wherein the at least one reporter element is incorporated into the second constituent.

38. The method of claim 36, wherein the second constituent comprises an encoded particle comprising a sequence of colored layers, wherein the sequence provides the second code.

39. The method of claim 38, wherein the at least one reporter element is incorporated into the encoded particle.

* * * * *